United States Patent [19]

Terada et al.

[11] 4,326,414
[45] Apr. 27, 1982

[54] HUMIDITY DETECTING APPARATUS

[75] Inventors: Jiro Terada; Tsuneharu Nitta, both of Katana, Japan

[73] Assignee: Matsushita Electric Industrial Co., Ltd., Kadoma, Japan

[21] Appl. No.: 107,182

[22] Filed: Dec. 26, 1979

[30] Foreign Application Priority Data

Dec. 26, 1978 [JP] Japan .................. 53/165743
Jul. 31, 1979 [JP] Japan .................... 54/99177

[51] Int. Cl.³ .......................................... G01W 1/00
[52] U.S. Cl. .............................. 73/336.5; 338/35; 324/65 R
[58] Field of Search ................. 73/335, 336.5, 73; 338/35; 324/65 R

[56] References Cited

U.S. PATENT DOCUMENTS

| 2,740,293 | 4/1956 | Brady | 73/336.5 X |
| 4,011,538 | 3/1977 | Froemel | 338/35 |
| 4,015,230 | 3/1977 | Nitta | 338/35 |
| 4,017,820 | 4/1977 | Ross | 338/35 |
| 4,080,564 | 3/1978 | Nitta | 338/35 X |

FOREIGN PATENT DOCUMENTS 523338  8/1976  U.S.S.R. ..................... 73/336.5

Primary Examiner—James J. Gill
Attorney, Agent, or Firm—Wenderoth, Lind & Ponack

[57] ABSTRACT

A humidity detecting resistor porcelain element, with at least one portion of an electrode being made of a resistance heating unit and the electrode serving for the resistance heating unit and humidity detecting element, and a humidity detecting apparatus using the humidity detecting resistor porcelain element. The heating and cleaning operations of the humidity detecting resistor porcelain can be uniformly and efficiently performed, thus ensuring the stable humidity detection. Also, the circuit construction of the humidity detecting apparatus can be simplified. They can be provided for use in the detecting and controlling operations of the various humidities.

12 Claims, 9 Drawing Figures

HUMIDITY DETECTING APPARATUS

BACKGROUND OF THE INVENTION

The present invention relates to a humidity detecting element comprising a resistor, which sensitively detects the humidity to vary the electric resistance. The present invention provides a humidity detecting resistor porcelain element which is useful as a detecting terminal for a humidity regulator and a humidity detecting apparatus using the element.

A metallic oxide is generally superior in moisture absorption, which is used to make the humidity detecting resistor. The metallic oxide humidity detecting elements are known for use in aluminum oxide thin films through the surface oxidation of aluminum sheet, colloid grains, glazed thin films mixed with glass components and partially with porcelain. However, the thin film or the colloid grain elements involve surface deterioration due to contamination or hysteresis. The glazed thin film element is stable with respect to atmospheric conditions and is restricted only to applications involving high humidity. The porcelain element is improved so as to be sensitive to a considerably lower humidity than the glazed element, but is restricted in control to a relative humidity of 20% or more. It is recognized that the glazed or the porcelain element is preferred in terms of response, thermal stability and atmosphere resistance as the humidity detecting element in the conventional embodiments. Since they are sintered at the high temperatures of 1,000° C. or more, they are stable against the various atmospheres. For example, suppose that they are heated and cleaned at a time when the humidity detecting characteristics of the humidity detecting resistor have been removed due to the various gases (oil components), and they can be used semi-permanently. The heating system in the heating and cleaning operations is composed of a thermal radiation type wherein the humidity detecting resistor is heated through the radiated heat from a nearby-disposed resistance heating unit or is composed of a heat conduction type wherein a humidity detecting resistor is provided on the resistance heating unit through an insulating substratum to conduct the heat from the resistance heating through the insulating substratum to the humidity detecting resistor. However, in either of these cases, disadvantages such as an inferior thermal response, a longer response time, high consumption of power for the heating and cleaning operations, and more complicated construction were involved, whereby the use thereof was restricted. The present invention is created to provide a humidity detecting element free from the above-described conventional disadvantages.

SUMMARY OF THE INVENTION

Accordingly, an object of the present invention is to provide a humidity detecting resistor element which is useful as a detecting element for a humidity regulator.

Another object of the present invention is to provide a humidity detecting apparatus, using a humidity detecting resistor as above, provided with a power supply and a detecting means.

According to the present invention, a humidity detecting resistor element and a humidity detecting apparatus using the element are provided. In the humidity detecting resistor element, at least one portion of an electrode disposed on the humidity detecting resistor element is composed of a resistance heating unit and the electrode serves for the resistance heating unit and a humidity detecting electrode.

The humidity detecting apparatus comprises a humidity detecting resistor element wherein at least one portion of an electrode provided on the humidity detecting resistor element is composed of a resistance heating unit, a power source for supplying electric power to a portion composed of said resistance heating unit for said electrode in order to heat the portion, and a detecting means for detecting the resistance values of said humidity detecting resistor element.

BRIEF DESCRIPTION OF THE DRAWINGS

These and other objects, features, aspects and advantages of the present invention will become more apparent from the following detailed description of the present invention when taken in conjunction with the accompanying drawings, in which.

DESCRIPTION OF PREFERRED EMBODIMENTS

Figure 1:
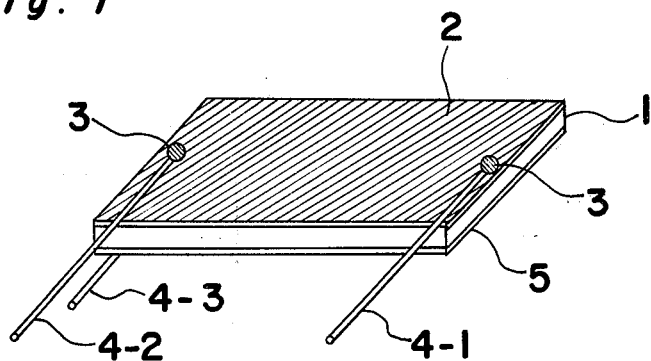
FIG. 1 is a perspective view of a humidity detecting unit in one embodiment of the present invention.

According to the present invention, $Cr_2O_3$, $TiO_2$ and MgO, each having a purity of 99.99% or more, are used as starting raw materials for the humidity detecting material to be blended into the composition in a ratio of MgO 65 by mol, $Cr_2O_3$ 65 by mol and $TiO_2$ 35 by mol. These blended materials were wet-mixed by a polyethylene pot with agate balls therein and were dried. Thereafter, they were molded in a square plate of $5\times4\times0.25$ mm under a pressure of 750 kg per $cm^2$, and the resultant molding was fired in air for two hours at 1,350° C. to make such a humidity detecting resistor element 1 as shown in FIG. 1. Then, resistance heating unit of a $RuO_2$ type paste was applied on the faces of the element 1 and was fired at 800° C. to form electrodes 2 and 5 on the both surfaces. Thereafter, lead wires 4-1, 4-2 and 4-3 each being made of Pt 90% and Ir 10% alloy of 0.1 mm in diameter were fired at 800° C., with the $RuO_2$ type paste 3, respectively, applied at the edges on the face of the electrode 2 and at one edge on the face of the electrode 5, and a humidity detecting unit comprising the detecting resistor element was obtained. Various humidity detecting resistor elements each having a face resistance are described in Table 1. The respective specimens shown in Table 1 are shown as a graph of FIG. 2 in terms of humidity-resistance characteristics.

TABLE 1

| Specimen No. | Face resistance ($\Omega/cm^2$) of resistance heating unit |
| --- | --- |
| 1 | 100 K |
| 2 | 10 K |
| 3 | 1 K |
| 4 | 100 |
| 5 | 10 |
| 6 | 1 |
| 7 | 0.1 |

Figure 2:
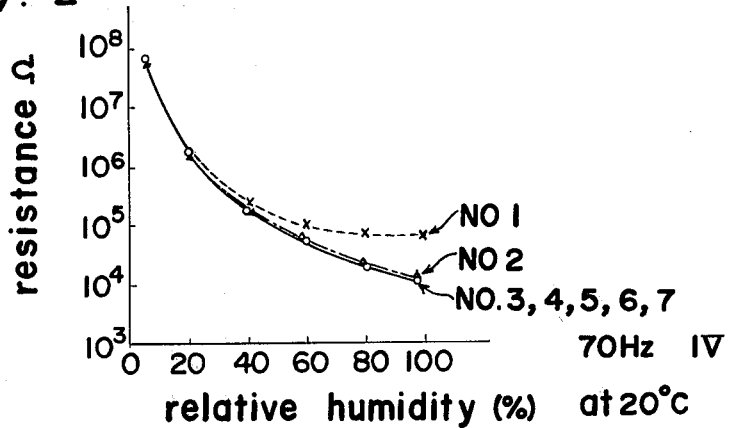
FIG. 2 is a humidity detection characteristic graph of the humidity detecting unit of FIG. 1.

Table 1 shows the relationship between the face resistance of the resistance heating unit of the humidity detecting resistor element and the specimens. FIG. 2 shows the characteristics of electric resistances (1 V-70 Hz) between electrodes 4-2 and 4-3 shown in FIG. 1 of the specimens shown in Table 1 when the relative humidity has been varied. According to FIG. 2, there are hardly any differences found among the No. 2, 3, 4, 5, 6 and 7 specimens. However, in the specimen No. 1, the resistance values with respect to the relative humidity variation hardly varies in the high humidity zone, whereby a deteriorated sensitivity results. The resistance values of the resistance heating unit are satisfactory in practical use if the resistance values are selected, as an upper limit, to an extent where the resistance values on the high humidity side of the humidity detecting resistor become approximately equal to half the resistance values on the low humidity side thereof. Also, in the No. 7 specimen, the humidity distribution is extremely poor in the central portion and end portions of the specimen after the heating and cleaning operations of the humidity resistor element. When the humidity detecting resistor element was contaminated with organic gases such as oil-component gases, the heating and cleaning operations were performed through the current flowing into the resistance heating unit, thus resulting in the producing of some portions being heated and cleaned and other portions not being heated and cleaned. This is because the temperature distributing condition is considered to become deteriorated due to Joule's heat when the resistances caused in the lead wire mounting portions of the resistance heating unit are higher than the resistance value of the resistance heating unit. To increase the temperature of the element to a heating and cleaning temperature of about 450° C., the applied current increases when the face resistance of the resistance heating unit is 1 $\Omega/cm^2$ or less, and the electrode of resistance heating unit is likely to peel off from the humidity detecting resistor element. When a dew forming cycle is performed, i.e., where the current flows to the resistance heating unit of the humidity detecting resistor element to test the life of the dew forming cycle and the drying cycle while the heating and cleaning operations are being performed, the humidity detecting characteristics are likely to be deteriorated to provide inferior heating and cleaning effects. As described hereinabove, the present invention provides an element wherein at least one portion of an electrode disposed on the humidity detecting resistor element is composed of a resistance heating unit and the electrode serves for the resistance heating unit and the humidity detecting electrode. The humidity detection uses the characteristics, i.e., the relative humidity-resistance characteristics, between the lead terminals 4-2 and 4-3. Also, the heating and cleaning operations are performed while the current is flowing between the lead terminals 4-1 and 4-2.

As the humidity detecting resistor element, electrolyte such as lithium chloride or the like, organic material, or metallic oxide series may be provided. However, the electrolyte series is not preferable, since it dissolves in high humidity. Also, the organic high molecular series cannot be used at high temperatures of approximately 80° C. or more because of heat-resisting problem. The metallic oxide series is considerably stable, including the heat resisting property, since the ceramic types can be easily provided due to the recent ceramic techniques. If oils, dusts or the like are absorbed and adhered upon the humidity detecting resistor element, the heating operation to the temperatures of approximately 400° C. or more easily removes them for reproducing proper operation thereof. In addition to the elements described in the above embodiment as the humidity detecting resistor element of the present invention, among the metallic oxides series, metallic oxides containing at least one component selected from a group of $Cr_2O_3$, $Fe_2O_3$, $NiO$, $ZnO$, $SnO_2$, $TiO_2$, $Al_2O_3$, $MgO$, $In_2O_3$, $MnO_2$, $CuO$, $CoO$, $MgCr_2O_4$, $FeCr_2O_4$, $NiCr_2O_4$, $MnCr_2O_4$, $CuCr_2O_4$, $CoCr_2O_4$, $Zn_2TiO_4$, $Zn_2SnO_4$, $Mg_2TiO_4$, $Mg_2SnO_4$, $BaTiO_3$, $PbZrO_3$, $CaTiO_3$, $KNbO_3$, $KTaO_3$, $PbTa_2O_6$, $NaNbO_3$, $LiNbO_3$, $LiTaO_3$, $PbHfO_3$, $BaTiO_3$, $SrTiO_3$ and components represented in $ABO_3$, wherein A is Pb, B indicates either one of $(Mg_{\frac{1}{3}}W_{\frac{2}{3}})$, $(Cd_{\frac{1}{3}}W_{\frac{2}{3}})$, $(Co_{\frac{1}{3}}W_{\frac{2}{3}})$, $(Sc_{\frac{1}{2}}Nb_{\frac{1}{2}})$, $(Fe_{\frac{1}{2}}Nb_{\frac{1}{2}})$, $(In_{\frac{1}{2}}Nb_{\frac{1}{2}})$, $(Yb_{\frac{1}{2}}Nb_{\frac{1}{2}})$, $(Ho_{\frac{1}{2}}Nb_{\frac{1}{2}})$, $(Fe_{\frac{1}{2}}Ta_{\frac{1}{2}})$, $(Sc_{\frac{1}{2}}Ta_{\frac{1}{2}})$, $(Lu_{\frac{1}{2}}Nb_{\frac{1}{2}})$, $(Lu_{\frac{1}{2}}Ta_{\frac{1}{2}})$, $(Mg_{\frac{1}{3}}Nb_{\frac{2}{3}})$, $(Zn_{\frac{1}{3}}Nb_{\frac{2}{3}})$, $(Co_{\frac{1}{3}}Nb_{\frac{2}{3}})$, $(Ni_{\frac{1}{3}}Nb_{\frac{2}{3}})$, $(Mg_{\frac{1}{3}}Ta_{\frac{2}{3}})$, $(Co_{\frac{1}{3}}Ta_{\frac{2}{3}})$, $(Ni_{\frac{1}{3}}Ta_{\frac{2}{3}})$, $(Fe_{\frac{2}{3}}W_{\frac{1}{3}})$ or $(Mn_{\frac{2}{3}}W_{\frac{1}{3}})$, are selected particularly as the preferable ones. These materials, which are thermally stable, are provided with humidity-resistance characteristics across the entire humidity zone, have faster response properties, longer service life and reproducing performance through the heating and cleaning than other materials. In addition, the preferable humidity detecting resistor elements include types containing a component 98 to 99.95 by weight composed of $Cr_2O_3$ in an amount of from 80 to 99.99 mol % and at least one type of material in an amount of from 0.01 to 20 mol % selected from a group consisting of $TiO_2$, $ZrO_2$, $HfO_2$, $SnO_2$, $Nb_2O_5$, $Ta_2O_5$, $CeO_2$, $WO_3$, $MnO_2$, $MoO_2$, $DyO_2$, $V_2O_5$, $SiO_2$, $GeO_2$, and at least one type of component in an amount of from 0.05% to 2% by weight selected from a group consisting of $BeO$, $MgO$, $CaO$, $SrO$, $BaO$, $FeO$, $NiO$, $CuO$, $ZnO$, $CdO$, $PbO$. Also preferable are materials containing at least one type of material in an amount of from 1 to 99 mol % selected from a group consisting of $MgCr_2O_4$, $FeCr_2O_4$, $NiCr_2O_4$, $CoCr_2O_4$, $MnCr_2O_4$, $CuCr_2O_4$, $Mg_2TiO_4$, $Mg_2SnO_4$, $Zn_2SnO_4$ and at least one type of material in an amount of from 1 to 29 mol % selected from a group consisting of $TiO_2$, $ZrO_2$, $HfO_2$ and $SnO_2$. Also, when the average air hole diameter of the resistance heating unit is 10 μm or more, the humidity detecting resistance characteristics becomes generally higher with respect to the relative humidity of the humidity detecting resistor element to provide a high impedance, thus making it difficult to detect the humidity in a low ambient humidity. At the heating and cleaning operations, the thermal conduction becomes so small that the heating and cooling operations are hard to be performed. Accordingly, the average air hole diameter of the electrode of resistance heating unit mounted on the humidity detecting resistor element is preferred to be 10 μm or less. The thickness of the resistance heating unit was preferred to be 0.1 to 50 μm in terms of not only thermal stability, i.e., stability in thermal expansion, peel-off or the like, but humidity response property or the like. In addition, the preferred components for the resistance heating unit are of a type containing at least one type selected from a group consisting of metals and alloys each having silver, nickel, zinc, chromium, palladium, gold, platinum, tin, aluminum, indium as major component; metal oxides having nickel oxide, zinc oxide, indium oxide, ruthenium oxide as major component; and semiconductors. When the above-described materials are used for the resistance heating unit and electrode material, the resultant device has humidity characteristics, cementing stability with the humidity detecting element and moisture deabsorbing properties which are superior.

As described hereinabove, the present invention provides a humidity detecting resistor element wherein at least one portion of an electrode provided on the humidity detecting resistor element is composed of a resistance heating unit and the electrode serves for the resistance heating unit and the humidity detecting electrode. According to the present invention, the construction of the humidity detecting unit in comparison with prior art devices is extremely simplified, and thus its size can be easily made smaller, resulting in its thermal capacity being smaller and its thermal response time being shorter. Also, less power is consumed during the heating and cleaning operations for the humidity detecting unit. Since the resistance heating unit and the humidity detecting apparatus for the humidity detecting resistor element are used in common, the humidity detecting portion can be uniformly heated, thus ensuring the effectiveness of the cleaning operation. When the humidity detecting resistor element, which is provided on a cooker, becomes dirty, the quick heating and cleaning operations can be performed to restore the original humidity detecting property.

As described hereinabove, the humidity detecting resistor element of the present invention is superior in durability, stably retaining accuracy in heating repetition tests. In addition, since the construction is extremely simplified, the mechanical strength is superior and the manufacturing cost is lower.

Figure 3:
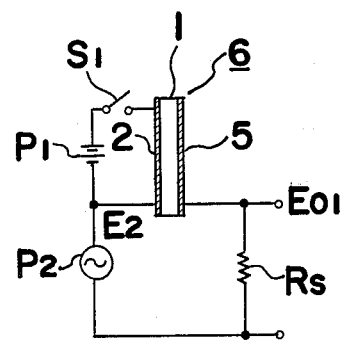
FIG. 3 is an electric circuit diagram showing one embodiment of a humidity detecting apparatus of the present invention.

And then, the humidity detecting apparatus using the humidity resistor element will be described hereinafter. FIG. 3 shows the circuit construction of a humidity detecting apparatus in one embodiment of the present invention, wherein reference numeral 6 is a humidity detector including a humidity detecting resistor element 1 constituted as mention above. A power supply P1 (direct current 5 V) for use in the heating and cleaning operation is connected through a switch S1 so that the electric current may be supplied from the power supply P1 to one electrode 2 of the humidity detector 6. One terminal of a power supply P2 (output voltage E2, 60 Hz, 1 V) is connected to the electrode 2 of the humidity detector 6 in common to one terminal of the power supply P1, and the other terminal of the power supply P2 is connected to the other electrode 5 of the humidity detector 6 through a resistor Rs (100 KΩ) for the output detecting application. Output Eo1 is measured across the resistor Rs. In a humidity detecting apparatus of such an arrangement, the switch S1 is closed to allow the current to flow along its face direction to the electrode 2 and the electrode 2 is heated due to the operation of the resistance heating unit to heat the humidity detecting resistor element 1 to perform the cleaning operation. The switch S1 is opened to end the cleaning operation.

The resistance value $(E2-Eo1)Rs/Eo1$ of the element 1 is found from the output Eo1 measured across the resistor Rs and the relative humidity becomes apparent from the resistance value.

Figure 4:
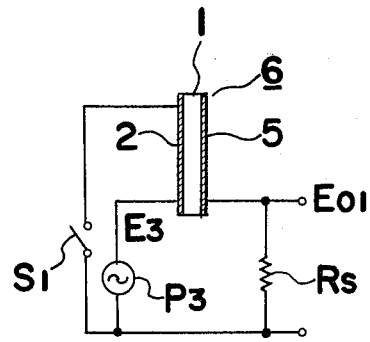
FIG. 4 shows another embodiment of a humidity detecting apparatus similar to FIG. 3.

FIG. 4 shows the circuit diagram of humidity detecting apparatus in another embodiment of the present invention. In this case, one power supply P3, i.e., output voltage E3 in FIG. 4, serves for the heating and cleaning application and the humidity detecting application, in place of the two power supplies P1 and P2 used in FIG. 3. In FIG. 4, the same reference numerals are given to the components in common with those in FIG. 3 and the description thereof are omitted for the sake of brevity.

The humidity detecting apparatus of such constructions as described hereinabove were not deteriorated in performance, and the measured humidity detecting accuracy was within ±1% of actual relative humidity in a test where the heating and cleaning operations (heating power 1.6 watt) were repeated 100,000 times or more.

It is to be noted that the humidity detecting apparatus can provide the same effects so far as the humidity detecting resistor elements, as described hereinbefore are employed, wherein at least one portion of an electrode provided on a humidity detecting resistor element is composed of a resistance heating unit, and the electrode serves for said resistance heating unit and a humidity detecting electrode.

Also, in the humidity detecting apparatus, the humidity can be automatically controlled if the controlling system for an air conditioning machine is connected to the output side. The humidity detecting characteristics of the humidity detecting resistor element and the resistance values of the detecting resistor Rs are properly combined to vary the humidity detecting range. An AC power supply will do as the heating power supply P1 in FIG. 3. Also, the heating resistor forming the electrode must be designed so that the resistance values may enable approximately a 450° C. rise in temperature due to heating.

According to the present invention, the humidity detecting unit in comparison to prior art devices is extremely simplified in construction and, thus, the size can be easily made smaller, whereby the thermal capacity thereof becomes smaller and the thermal response time becomes shorter in addition to a reduction in the power consumed for the heating and cleaning operations. Also, since the humidity detecting resistor element and the resistance heating unit are integrated as one unit, the humidity detecting portion can be uniformly heated, ensuring facility in the cleaning operation. When the humidity detecting resistor element, which is provided on the cooker, has become dirty, the quick heating and cleaning operations can be performed to recover the original humidity detecting characteristics.

Also, the humidity detecting apparatus of the present invention is superior in durability because of the stable retention of the accuracy in the heating repetition tests. Furthermore, since the construction is extremely simplified as described hereinabove, the mechanical strength is superior and the manufacturing cost is lower.

In the humidity detecting apparatus of the present invention, the power supply for heating operation and humidity detecting operation can be used in common and thus the circuit construction can be simplified.

A resistor or a capacitor (condenser) is inserted across the terminals of a portion composed of the resistance heating unit. A split intermediate point terminal is provided at an intermediate portion of the resistor or the capacitor (condenser) to be divided in two. The humidity detecting apparatus is provided with a detecting means, which detects the resistance values of the humidity detecting resistor element between the electrode disposed on the humidity detecting resistor element and the split intermediate point terminal of the resistor or the capacitor.

Figure 5:
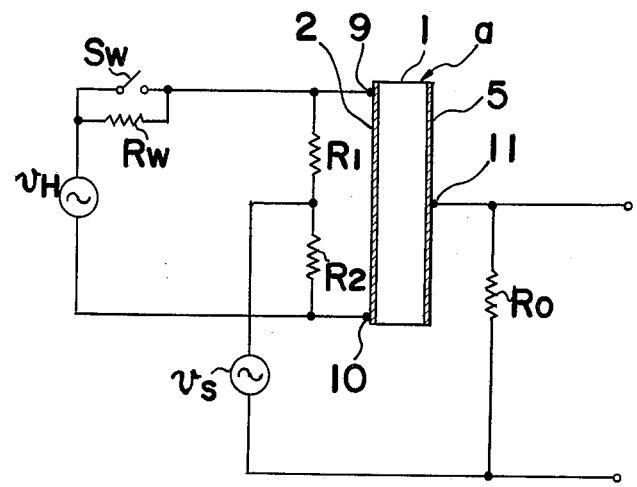
FIG. 5 shows the other embodiment of a humidity detecting apparatus similar to FIG. 4.
Figure 6:
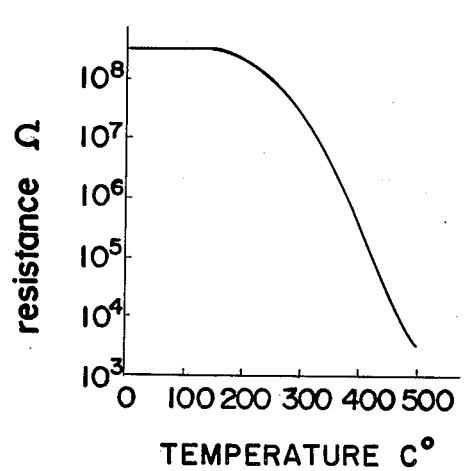
FIG. 6 shows a thermistor characteristic graph of a humidity detecting resistor element employed in the apparatus of FIG. 5.
Figure 7:
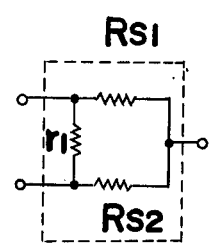
FIG. 7 is an equivalent circuit diagram of the humidity detecting resistor element employed in the apparatus of FIG. 5.

In FIG. 5, the electric signals from a heater power supply are not mixed with the humidity detecting signals even when the dew forming prevention and the reference humidity level variation which shifts the relative humidity of the measured humidity atmosphere, have been performed. The auxiliary heating of the humidity detecting resistor element is referred to as indirect heating. Also, in the heating and cleaning operation, thermistor characteristics (400° C. to 500° C.) of the humidity detecting resistor element as described hereinbefore may be used to control the heating and cleaning temperatures. For example, the thermistor characteristics, as shown in FIG. 6, of the humidity detecting resistor element having a composition in a ratio of MgO 65 by mol, $Cr_2O_3$ 65 by mol and $TiO_2$ 35 by mol described in the above-described embodiment is used for the following description. The humidity detecting resistor element "a" in FIG. 5, if equivalently represented, can be shown by an electric circuit of FIG. 7, wherein reference characters Rs1 and Rs2 represent, respectively, the resistance values of the humidity detecting resistor element between the respective contacts 9 and 11, and contacts 10 and 11, and reference character r represents the resistance value of the resistance heating unit 3. In FIG. 5, an impressed power supply $V_S$ is provided for detecting the humidity, a power supply $V_H$ for the heating and cleaning operation and the indirect heating operation, and a resistor Ro for detecting the humidity. A resistor Rw is adapted to control the current flowing to the resistance heating unit to thereby perform the indirect heating operation. During the indirect heating operation, a voltage $V_{N1}$, wherein the power supply $V_H$ for the indirect heating operation is represented as noise in a humidity detecting circuit loop composed of Vs, R1·R2, humidity detecting resistor element and Ro, is calculated from the following equation (1).

$$\frac{\frac{r(R1+R2)}{(R1+R2)+r}}{\frac{r(R1+R2)}{(R1+R2)+r}+Rw} \cdot V_H \cdot \left(\frac{R2}{R1+R2}-\frac{Rs2}{Rs1+Rs2}\right)=V_{N1} \quad (1)$$

wherein R1, R2<<Rs1, Rs2 is established. $V_{N1}=0$ is established if the conditions of R1=R2 and Rs1=Rs2 are substituted into the above equation, thus preventing the power supply during the indirect heating operation from being mixed into the temperature detecting circuit loop. Also, when the humidity detecting resistor element has been heated and cleaned, the resistance values decrease and the resistance values of Rs1 and Rs2 decrease due to the resistance-humidity characteristics as shown in FIG. 6. As the indirect heating operation, the conditions of R1=R2, Rs1=Rs2 are substituted into the equation, $V_{N1}=0$ is established to prevent the indirect heating and heating, and cleaning power supply from being mixed into the humidity detecting circuit system. As the resistances of Rs1 and Rs2 decrease as shown in FIG. 6 during the heating and cleaning operations, where the switch Sw is turned on, a signal is generated across the resistor Ro of the humidity detecting circuit loop. For example, when the controlling operation is required to be performed at the cleaning temperature 450° C. of the humidity detecting resistor element, it should detect the signals across the resistor Ro when the resistance value of the Y axis has become 15 KΩ at the X axis 450° C. of FIG. 6, to thereby turn off the switch Sw of FIG. 5 and the heating and cleaning operations can be performed. To turn off the switch Sw, it is preferable to provide a voltage comparator and set a reference value of the voltage comparator to actuate the comparator when the humidity detecting resistor element reaches 450° C. Also, it is preferable to detect the output signal of the voltage comparator of the above-described circuit in order to turn off the switch Sw.

Figure 8:
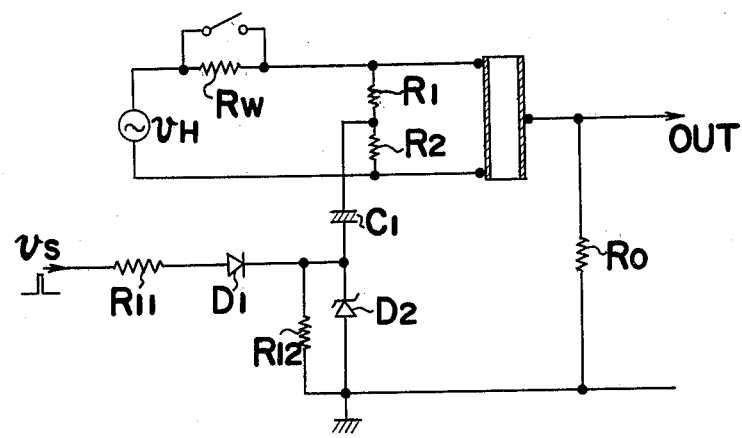
FIG. 8 is a circuit diagram showing the further embodiment of the humidity detecting apparatus of the present invention.
Figure 9:
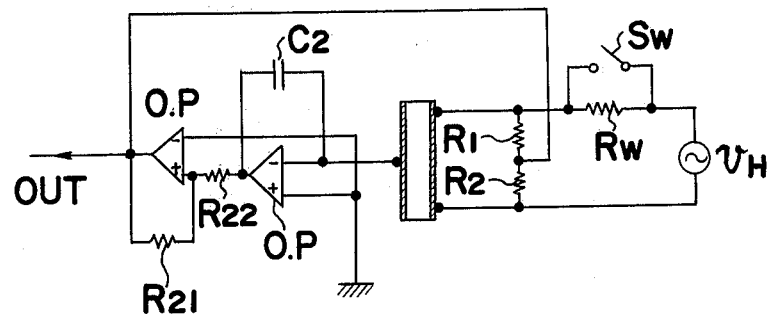
FIG. 9 is a similar diagram to FIG. 8 showing another further embodiment of the present invention.

FIG. 5 shows that the power supply used during the indirect heating operation and the heating and cleaning operation may not be mixed into the humidity detecting circuit, and in the humidity detecting signal, the output signal across resistor Ro corresponds to the humidity. The embodiments of the humidity detecting apparatus of the present invention are shown in FIG. 8 and FIG. 9, showing a pulse system and a frequency system as the examples for detection of the thermistor resistance value, as shown in FIG. 6, during the heating and cleaning operation or for detection of the voltage supply humidity. FIG. 8 shows a pulse circuit wherein the Vs shown in FIG. 5 is composed of R11, R12, D1, D2 and C1. In the pulse circuit, a pulse voltage is put into the input signal, and the detecting signal of the cleaning temperature during the heating and cleaning operations and the humidity detecting signal corresponding to the humidity can be detected respectively at the output terminals, i.e., across the resistor Ro terminals. In FIG. 9, the resistance changes of the humidity resistor element are converted into frequencies with an oscillator composed of R21, R22, C2 and operational amplifiers. The frequency system of FIG. 9 can detect the detecting signals of the cleaning temperatures during the heating and cleaning operations and the humidity detecting signals corresponding to the humidity. Referring to FIG. 5, satisfactory results are available even in the service life tests, i.e., continuous tests of 100,000 times or more in heating and cleaning cycle test within 0 to 100%±1% in humidity detecting accuracy, wherein R1=1 KΩ, R2=1 KΩ, resistor heating unit resistance 3=25Ω, Rw=1 KΩ, Ro=100 KΩ, $V_H$=6.5 V and $V_S$=1 V. According to the humidity detecting apparatus of the present invention as described hereinabove, the reliable heating and cleaning operations can be performed, since the humidity detecting resistor element itself functions as a temperature sensor. The humidity detecting apparatus of the present invention is extremely simplified in circuit construction as compared with the humidity detecting apparatus provided with a temperature detector using a thermoelectric couple, thermistor or the like from the outside. When the oil or the like attached onto the surface of the humidity detecting element, the cleaning operation thereof can be performed through the heating operation and the heating operation can be automatically controlled, so that the element is not damaged due to the heating and cleaning operations. Therefore, the present invention can provide a humidity detecting apparatus which can perform the heating and cleaning operations and detect the humidity. According to the apparatus of the present invention, the voltage $V_H$ can be supplied by power supplies of AC, DC and pulse type, and the same results can be obtained even if R1 and R2 are replaced by capacitors to form the split intermediate point. Also, $R1=1/\omega c1$ and $R2=1/\omega c2$ and the constant of the humidity detecting resistor element shape, size and circuit resistance values are restricted.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A humidity detecting apparatus for measuring ambient humidity and having a humidity detecting resistor element comprising:
   a humidity detecting portion of a metallic oxide material whose resistance is related to said ambient humidity and having first and second electrodes on opposite sides thereof;
   said first electrode having first and second terminals and of a resistive material, wherein when an electrical current is passed between said first and second terminals, said first electrode operates as a resistance heating unit to thereby heat said humidity detecting resistor element; and
   said second electrode having a third terminal arranged such that said resistance of said humidity detecting portion is measured between said first and third terminals to thereby determine said ambient humidity.

2. A humidity detecting apparatus as defined in claim 1, wherein said humidity detecting resistor element has, as major component, component represented in at least either one of $Cr_2O_3$, $FeO_3$, NiO, ZnO, $SnO_2$, $TiO_2$, $Al_2O_3$, MgO, $In_2O_3$, $MnO_2$, CuO, CoO, $MgCr_2O_4$, $FeCr_2O_4$, $NiCr_2O_4$, $MnCr_2O_4$, $CuCr_2O_4$, $CoCr_2O_4$, $Zn_2TiO_4$, $Zn_2SnO_4$, $Mg_2TiO_4$, $Mg_2SnO_4$, $BaTiO_3$, $PbZrO_3$, $CaTiO_3$, $KNbO_3$, $KTaO_3$, $PbTa_2O_6$, $NaNbO_3$, $LiNbO_3$, $LiTaO_3$, $PbHfO_3$, $SrTiO_3$ and $ABO_3$, wherein A is Pb, B contains at least one selected from $(Mg_{\frac{1}{3}}W_{\frac{2}{3}})$, $(Cd_{\frac{1}{3}}W_{\frac{2}{3}})$, $(Co_{\frac{1}{3}}W_{\frac{2}{3}})$, $(Sc_{\frac{1}{2}}Nb_{\frac{1}{2}})$, $(Fe_{\frac{1}{2}}Nb_{\frac{1}{2}})$, $(In_{\frac{1}{2}}Nb_{\frac{1}{2}})$, $(Yb_{\frac{1}{2}}Nb_{\frac{1}{2}})$, $(Ho_{\frac{1}{2}}Nb_{\frac{1}{2}})$, $(Fe_{\frac{1}{2}}Ta_{\frac{1}{2}})$, $(Sc_{\frac{1}{2}}Ta_{\frac{1}{2}})$, $(Lu_{\frac{1}{2}}Nb_{\frac{1}{2}})$, $(Lu_{\frac{1}{2}}Ta_{\frac{1}{2}})$, $(Mg_{\frac{1}{3}}Nb_{\frac{2}{3}})$, $(Zn_{\frac{1}{3}}Nb_{\frac{2}{3}})$, $(Co_{\frac{1}{3}}Nb_{\frac{2}{3}})$, $(Ni_{\frac{1}{3}}Nb_{\frac{2}{3}})$, $(Mg_{\frac{1}{3}}Ta_{\frac{2}{3}})$, $(Co_{\frac{1}{3}}Ta_{\frac{2}{3}})$, $(Ni_{\frac{1}{3}}Ta_{\frac{2}{3}})$, $(Fe_{\frac{2}{3}}W_{\frac{1}{3}})$ and $(Mn_{\frac{2}{3}}W_{\frac{1}{3}})$.

3. A humidity detecting apparatus as defined in claim 1, wherein said humidity detecting resistor element is composed of a component in the amount of from 98 to 99.5% by weight composed of $Cr_2O_3$ in the amount of from 80 to 99.99 mol % and at least one type of material in the amount of from 0.01 to 20 mol % selected from a group consisting of $TiO_2$, $ZrO_2$, $HfO_2$, $SnO_2$, $Nb_2O_5$, $Ta_2O_5$, $CeO_2$, $WO_3$, $MnO_2$, $MoO_2$, $DyO_2$, $V_2O_5$, $SiO_2$ and $GeO_2$, and a component in the amount of from 0.05 to 2% by weight composed of at least one type selected from a group consisting of BeO, MgO, CaO, SrO, BaO, FeO, NiO, CuO, ZnO, CdO, PbO.

4. A humidity detecting apparatus as defined in claim 1, wherein said humidity detecting resistor element is composed of at least one type of material in the amount of from 1 to 99 mol % selected from a group consisting of $MgCr_2O_4$, $FeCr_2O_4$, $NiCr_2O_4$, $CoCr_2O_4$, $MnCr_2O_4$, $CuCr_2O_4$, $Mg_2TiO_4$, $Mg_2SnO_4$, $Zn_2SnO_4$, and at least one type of material in the amount of from 1 to 99 mol % selected from a group consisting of $TiO_2$, $ZrO_2$, $HfO_2$ and $SnO_2$.

5. A humidity detecting apparatus as defined in claim 1, wherein the average air hole diameter of said resistance heating unit is less than or equal to 10 $\mu$m.

6. A humidity detecting apparatus as defined in claims 1 or 5, wherein said resistance heating unit includes at least one type of material selected from a group consisting of metals and alloys among silver, nickel, zinc, chromium, palladium, gold, platinum, tin, aluminum, indium, and of metal oxides among nickel oxide, zinc oxide, indium oxide, ruthenium oxide, as major component.

7. A humidity detecting apparatus as defined in claims 1 or 5, wherein the thickness of said resistance heating unit is in the range of 0.1 to 50 $\mu$m.

8. A humidity detecting apparatus as defined in claim 7, wherein said resistance heating unit includes at least one type of material selected from a group consisting of metals and alloys among silver, nickel, zinc, chromium, palladium, gold, platinum, tin, aluminum, indium, and of metal oxides among nickel oxide, zinc oxide, indium oxide, ruthenium oxide, as major component.

9. A humidity detecting apparatus for measuring ambient humidity and having a humidity detecting element comprising:
   a humidity detecting portion of a metallic oxide material whose resistance is related to said ambient humidity and having first and second electrodes on opposite sides thereof;
   said first electrode having first and second terminals and of a resistive material, wherein when an electrical current is passed between said first and second terminals, said first electrode operates as a resistance heating unit to thereby heat said humitidy detecting resistor electrode;
   a series connected pair of impedances connected between said first and second terminals and having a junction point therebetween; and
   said second electrode having a third terminal arranged such that said resistance of said humidity portion is measured between said junction point and said third terminal to thereby determine said ambient humidity.

10. A humidity detecting apparatus as defined in claim 9, wherein said pair of impedances comprise a pair of resistors.

11. A humidity detecting apparatus as defined in claim 9, wherein said pair of impedances comprise a pair of capacitors.

12. A humidity apparatus as defined in claims 9 or 10 or 11, wherein said pair of impedances are equal in value, whereby the voltage between said junction point and said third terminal is independent of said electrical current passing through said resistance heating unit.

* * * * *